US012697158B2

(12) United States Patent
Mahrouche et al.

(10) Patent No.: US 12,697,158 B2
(45) Date of Patent: Aug. 4, 2026

(54) DELIVERING REFRIGERANT TO CATHETERS FOR CRYOTHERAPY

(71) Applicant: Medtronic CryoCath LP, Toronto (CA)

(72) Inventors: Rachid Mahrouche, Cote St-Luc (CA); Gilles Desrochers, Beaconsfield (CA); Wing-Choi Ma, Maple Grove, MN (US); Julia A. Schraut, Shoreview, MN (US); Bertin Simeon, Laval (CA); Scott A. Hareland, Lino Lakes, MN (US)

(73) Assignee: Medtronic CryoCath LP, Toronto (CA)

( * ) Notice: Subject to any disclaimer, the term of this patent is extended or adjusted under 35 U.S.C. 154(b) by 580 days.

(21) Appl. No.: 18/317,499

(22) Filed: May 15, 2023

(65) Prior Publication Data

US 2023/0389976 A1 Dec. 7, 2023

Related U.S. Application Data

(60) Provisional application No. 63/349,249, filed on Jun. 6, 2022.

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00744* (2013.01);
(Continued)

(58) Field of Classification Search
CPC ............ A61B 18/02; A61B 2018/0022; A61B 2018/00744; A61B 2018/00791;
(Continued)

(56) References Cited

U.S. PATENT DOCUMENTS 3,823,575 A * 7/1974 Parel ...................... A61B 18/02
606/24
6,887,234 B2 5/2005 Abboud et al.
(Continued)

FOREIGN PATENT DOCUMENTS

EP 3998031 A1 5/2022
WO 20210026467 A1 2/2021

OTHER PUBLICATIONS

European Patent Office Extended Search Report for Application No. 23176814.4 dated Oct. 10, 2023 (11 pages).

*Primary Examiner* — Niketa Patel
*Assistant Examiner* — Joshua Brendon Solomon
(74) *Attorney, Agent, or Firm* — Michael Best & Friedrich LLP

(57) ABSTRACT

A method and system for controlling flow of refrigerant through a medical device are disclosed. According to one aspect, a system for delivering refrigerant to an expansion cavity portion of the medical device comprises a first path and a second path in communication with the expansion cavity portion. The system also includes a first PID controller in communication with a first proportional valve in the first path, the first PID controller being configured to operate the first proportional valve based on a pressure measurement in the first path; and a second PID controller in communication with a second proportional valve in the second path, the second controller being configured to operate the second proportional valve based on a pressure measurement in the second path or in the expansion cavity portion.

18 Claims, 6 Drawing Sheets

(52) U.S. Cl.
CPC .............. *A61B 2018/00791* (2013.01); *A61B 2018/00863* (2013.01); *A61B 2018/0212* (2013.01); *A61B 2018/0262* (2013.01)

(58) Field of Classification Search
CPC .. A61B 2018/00863; A61B 2018/0212; A61B 2018/0262; A61B 2018/00011; A61B 2018/00023; A61B 2018/00214; A61B 2018/00577; A61B 2018/00636; A61B 2018/00666; A61B 2018/00684; A61B 2018/00773; A61B 2018/00839; A61B 2018/00988
See application file for complete search history.

(56) References Cited

U.S. PATENT DOCUMENTS

| | | | |
|---|---|---|---|
| 6,887,237 B2 | 5/2005 | McGaffigan | |
| 8,545,491 B2 | 10/2013 | Abboud et al. | |
| 2005/0215989 A1 | 9/2005 | Abboud et al. | |
| 2007/0032783 A1* | 2/2007 | Abboud ................. | A61B 18/02 606/22 |
| 2010/0042086 A1 | 2/2010 | Reynolds | |
| 2016/0008049 A1* | 1/2016 | Mahrouche ............ | A61B 18/02 606/21 |
| 2018/0036057 A1 | 2/2018 | Abboud et al. | |
| 2019/0336192 A1 | 11/2019 | Lalonde et al. | |

* cited by examiner

DELIVERING REFRIGERANT TO CATHETERS FOR CRYOTHERAPY

CROSS-REFERENCE TO RELATED APPLICATION

This application claims the benefit of U.S. Provisional Patent Application No. 63/349,249, filed 6 Jun. 2022, and entitled "METHOD AND APPARATUS FOR INFLATING BALLOON CATHETERS FOR CRYOTHERAPY."

FIELD

This application relates generally to methods and apparatus for managing delivery of refrigerants to medical devices, and more particularly but not exclusively, to cryoablation and cryomapping.

BACKGROUND

Cryoablation is a process that uses extreme cold to destroy tissue. In various examples, cryoablation is performed using a hollow conduit (e.g., a cryoprobe or cryoablation catheter) through which a cooled, thermally conductive fluid is circulated. The cryoprobe is positioned adjacent to a target area in the body in such a way that the delivered cold ablates the tissue in the target area.

Cryomapping is typically used complementarily to cryoablation. In an example application, cryomapping is performed to confirm target sites for cryoablation. When the cell temperatures do not fall below a certain (low) temperature, the cold-induced physiological changes are mostly reversible, and the cells recover their precooling function when warmed. In the electrophysiology laboratory, temporary changes induced by the cryoprobe during cryomapping are detected and evaluated to judge the efficacy and/or safety of the prospective cryoablation.

SUMMARY

Disclosed herein are, among other things, various examples, aspects, features, and embodiments of systems and methods for controllable delivery of pressurized refrigerant to a medical device, such as a cryoablation catheter. In some examples, a refrigerant delivery system includes an expansion cavity portion and a first path and a second path in communication with the expansion cavity portion. The refrigerant delivery system also includes a first proportional-integral-derivative (PID) controller in communication with a first solenoid valve in the first path. In some instances, the first PID controller is configured to operate the first solenoid valve based on a pressure measurement in the first path. The refrigerant delivery system also includes a second PID controller in communication with a second solenoid valve in the second path. The second controller is configured to operate the second solenoid valve based on a pressure measurement in the second path or in the medical device.

One example provides a system for delivering refrigerant to a medical device. The system includes a first path for delivering the refrigerant to an expansion cavity portion of the medical device from a refrigerant source, the first path including a first solenoid valve. The system also includes a second path for removing the refrigerant from the expansion cavity portion, the second path including a second solenoid valve and a vacuum pump connected to draw the refrigerant from the expansion cavity portion through the second solenoid valve. The system further includes and a control circuit including (i) a first controller to control the first solenoid valve based on a pressure measurement in the first path and further based on a first setpoint value and (ii) a second controller to control the second solenoid valve based on a pressure measurement in the second path or in the expansion cavity portion and further based on a second setpoint value.

Another example provides a method of delivering refrigerant to a medical device. The method includes providing a first path for delivering the refrigerant to an expansion cavity portion of the medical device from a refrigerant source, the first path including a first solenoid valve. The method also includes providing a second path for removing the refrigerant from the expansion cavity portion, the second path including a second solenoid valve and a vacuum pump connected to draw the refrigerant from the expansion cavity portion through the second proportional valve. The method also includes controlling, with a control circuit, the first solenoid valve based on a pressure measurement in the first path and further based on a first setpoint value. The method further includes controlling, with the control circuit, the second solenoid valve based on a pressure measurement in the second path or in the expansion cavity portion and further based on a second setpoint value.

BRIEF DESCRIPTION OF THE DRAWINGS

Various example, aspects, features, and embodiments will be better understood by reference to the following detailed description when considered in conjunction with the accompanying drawings wherein.

DETAILED DESCRIPTION

Figure 1:
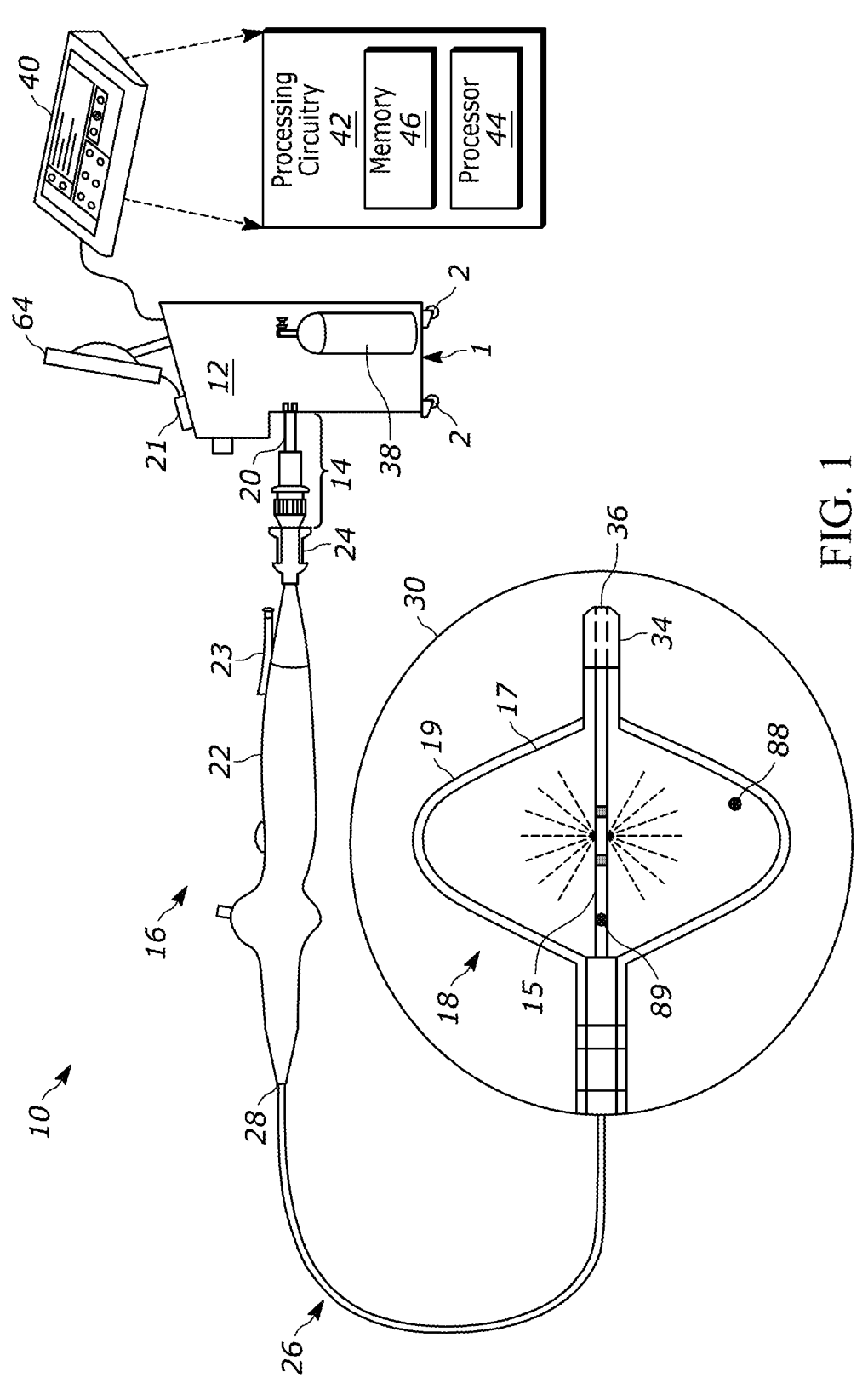
FIG. 1 is a schematic diagram illustrating a medical system according to various examples.

Catheter cryoablation is a technique that has applications in, for example, cancer, nerve, and cardiac treatment. In some examples, cryoablation is used to control heart rhythm by ablating certain tissues that cause abnormal heart rhythms. A cryoablation catheter is used to create lesions at locations where heat is removed thereby from cardiac cells by delivery of pressurized refrigerant, such as nitrous oxide ($N_2O$), with a controlled mass flow rate. Heat is transferred when the pressurized refrigerant expands and evaporates near the catheter tip. Cardiac cell lesions are created by the removal of heat from the tissue. Two types of catheters typically used for this type of procedure include: (i) a focal catheter, which has a rigid surface area, and (ii) a balloon catheter, which has an expandable, flexible surface area.

Catheter cryomapping is a focal catheter technique used to reversibly impair an action potential of cardiac cells without creating lesions. One purpose of this technique is to identify the effectiveness of potential locations for cryoablation prior to creating a lesion. Cryomapping is similar to cryoablation in that the catheter is placed at the target site where heat is removed from cardiac cells by the refrigerant. Cryomapping differs from cryoablation in that cryomapping is typically controlled through monitoring the catheter tip temperature and adjusting the flow of the refrigerant to maintain that temperature at a higher target value.

A console is provided to control the delivery of pressurized refrigerant. The console has a tank configured to hold the pressurized refrigerant. The pressure and temperature of the refrigerant at the distal end of the catheter are affected by the pressure and temperature of the refrigerant in the tank and by the configuration of various components located in or coupled to the refrigerant delivery pathways between the tank and the distal portion of the catheter.

In some cases, a balloon catheter may be inflated before initiating the treatment to allow the inflated balloon to be positioned in the desired anatomical region. Some consoles are configured to inflate the balloon by delivering a fixed volume of low-pressure refrigerant into the balloon catheter through a vacuum path of the catheter in a retrograde manner. The same vacuum path is then used during cryoablation to remove the expanded refrigerant from the catheter. Because this type of inflation uses a fixed volume of refrigerant, there is substantially no flow of the refrigerant once the inflation of the balloon is completed. Accordingly, the balloon pressure may begin to drop as soon as the last valve in the delivery path closes. In some cases, the pressure drop may be exacerbated by manipulation and/or movement (if any) directed at better positioning the catheter from an anatomical perspective. Disadvantageously, pressure changes (e.g., pressure drops) induced in this manner can adversely affect the treatment results.

In some other cases, a medical procedure may call for operating-mode changes, which typically affect the flow of the refrigerant within the system. One example is a change from an inflation mode, wherein the balloon is being inflated, to a treatment mode, wherein the balloon is being used in an approximately steady state of inflation to ablate the adjacent tissue. This operating-mode change typically produces a relatively large and abrupt change (e.g., reduction or increase) in the refrigerant flow rate. Disadvantageously, flow rate changes induced in this manner can create impediments to stable and reliable pressure control and can make it difficult to maintain the intended geometry and/or volume of the inflated balloon.

At least some of the above-indicated problems in the state of the art can beneficially be addressed using various methods and systems for managing refrigerant pressure and/or flow disclosed herein. For example, some embodiments overcome at least some of the above indicated problems by providing two or more separately controllable paths for the delivery and removal of the refrigerant to/from the balloon catheter. Various methods of operating such two or more paths are provided as well.

Before describing in detail various example embodiments, it should be noted that some embodiments reside primarily in combinations of apparatus components and processing steps related to control systems or circuits. Accordingly, components have been represented where appropriate by conventional symbols in the drawings, showing only those specific details that are pertinent to understanding the embodiments so as not to obscure the disclosure with details that will be readily apparent to those of ordinary skill in the pertinent art having the benefit of the description herein. Like numbers refer to like elements throughout the description.

It should be understood that various aspects disclosed herein may be combined in different combinations than the combinations explicitly presented in the description and accompanying drawings. It should also be understood that, depending on the example, certain acts or events of any of the processes or methods described herein may be performed in a different sequence, may be added, merged, or left out altogether (e.g., all described acts and/or events may not be necessary to carry out some of the techniques). In addition, while certain aspects of this disclosure are described as being performed by a single module or unit for purposes of clarity, it should be understood that the techniques of this disclosure may be performed by a combination of units or modules associated with, for example, a medical device.

FIG. 1 is a schematic diagram illustrating a medical system 10 according to various examples. The system 10 can be used for various cryotherapy procedures, including cryomapping and cryoablation, in different respective operating modes thereof. In the example shown, the system 10 includes a console 12 coupled to an umbilical system 14. The console 12 has wheels 2 attached to a base plate 1 thereof and, as such, is wheelable to different convenient locations in the treatment room. The umbilical system 14 is further coupled to a cryoablation catheter 16. In some examples, the cryoablation catheter 16 includes a suitable treatment device, such as a treatment device with a treatment portion 30, including an inflatable portion 18. In some other examples, the cryoablation catheter 16 has a different type of the treatment portion e.g., corresponding to a focal catheter design. In the example shown, the inflatable portion 18 has a double wall configuration and includes an outer balloon 19 and an inner balloon 17. The inner balloon 17 has a pressure sensor 88 therein. The inflatable portion 18 also includes a temperature sensor 89 placed in the return flow path of the refrigerant.

In some instances, the umbilical system 14 includes a coaxial cable umbilical 20 connected to the console 12 at one end thereof and to the cryoablation catheter 16 at the opposite end thereof. The coaxial cable umbilical 20 includes a refrigerant injection umbilical and a vacuum umbilical that provide respective inlet and return paths for the pressurized refrigerant used to cool the inflatable portion 18. The refrigerant injection umbilical can be used to transfer the pressurized refrigerant from the cryoablation console 12 to the cryoablation catheter 16. The vacuum umbilical can be used to allow the refrigerant, in liquid or gaseous state, to escape from the cryoablation catheter 16 back to the console 12.

In some instances, the catheter 16 includes a handle 22 having a coaxial connector 24 with both an injection lumen and a vacuum lumen therein. The catheter 16 further includes an elongated body 26 providing flow paths for the refrigerant between a proximal end 28 and the treatment portion 30 thereof. The treatment portion 30 includes a distal end 34. The distal end 34 includes a tip 36 with a lumen therein. In various examples, the tip 36 may or may not be highly thermally conductive. In some instances, the elongated body 26 is flexible to allow insertion into and passage through a natural orifice. In operation, pressurized refrigerant is injected into the injection umbilical within the elongated body 26 and delivered to an injection tube 15 within the inflatable portion 18 of the catheter 16. The vacuum umbilical within the elongated body 26 evacuates the refrigerant from the inflatable portion 18 back to the console 12. In various examples, the inflatable portion 18 has no electrodes or has at least one electrode configured to contact adjacent tissue and sense electrical activity thereat. It will be understood that the at least one electrode may be implemented in a variety of different shapes, sizes, and configurations.

When pressurized refrigerant is injected into the inflatable portion 18 via the elongated body 26, the inflatable portion 18 expands, causing at least some portions thereof to contact surrounding tissue. In addition to or in the alternative to the inflatable portion 18, the tip 36 is used to remove heat from the adjacent tissue to reach a first temperature for cryomapping and to reach a second temperature for cryoablation. The target temperature for the tip 36 is higher for cryomapping than for cryoablation, as indicated above. In various examples, a tank 38 holds pressurized nitrous oxide ($N_2O$) or another type of cooling gas, fluid, and/or liquid. The console 12 typically has internal piping or plumbing through which the refrigerant can be transferred from the tank 38 to the coaxial cable umbilical 20. In the distal portion 30 of the catheter 16, the pressurized refrigerant is released through the injection tube 15 inside the inflatable portion 18, which is typically held under a relatively low pressure, e.g., some degree of vacuum. Both the phase change from liquid to gas and expansion of the pressurized refrigerant are endothermic processes, which absorb heat, resulting in the catheter tip 36 and the inflatable portion 18 cooling down, in some cases to below freezing. The refrigerant vapor is returned from the catheter 16 through the vacuum path of the umbilical system 14 back to the console 12, where the vapor is evacuated and/or exhausted (also see FIG. 2).

An electronic controller 40 is included to control various functions of the catheter 16 and the console 12. In one example, the electronic controller 40 includes processing circuitry 42 illustrated in FIG. 1 using the correspondingly labeled expansion box. In the example shown, the processing circuitry 42 includes a memory 46 and a processor 44. The processor 44 is configured to access (e.g., write to and/or read from) the memory 46. In operation, the processing circuitry 42 controls, executes, and/or supports various functions, methods, and/or processes described herein. The memory 46 is configured to store data, programmatic software code, and/or other pertinent information described herein. Some pieces of the software include instructions that, when executed by the processor 44 and/or processing circuitry 42, cause the system 10 to perform various operations and processes described herein.

In various examples, various circuits of the electronic controller 40 are in communication with a user interface device 21 that enables an operator to operate the system 10 and input values of various control parameters, such as a target pressure for the delivery of pressurized refrigerant to the cryoablation catheter 16. In some examples, the user interface device 21 includes a keyboard and a mouse. A display device 64 connected to the user interface device 21 and to the electronic controller 40 is typically used to display various system parameters, such as temperatures and pressures at various locations in the system 10, e.g., the temperature in and near the tank 38 and the inflatable portion 18 and the pressure of the refrigerant at one or more locations along the delivery line and in the catheter 16.

In some examples, the console 12 supports a graphical user interface (GUI), e.g., presented on the user interface device 21 and/or the display device 64, which presents controls (for example, virtual buttons) to receive inputs from an operator of the console 12 to set the target pressure(s) and/or temperature(s) via a touch screen. For some procedures, the electronic controller 40 and/or the console 12 are configured to cycle through a sequence of temperature/pressure settings based at least in part on a plurality of target settings entered through the GUI. An example sequence of settings typically corresponds to successive time intervals. A timer included with the electronic controller 40 and/or the console 12 is used to appropriately clock the time intervals and/or to limit a time duration in which the system 10 is in some specific configuration.

Figure 2:
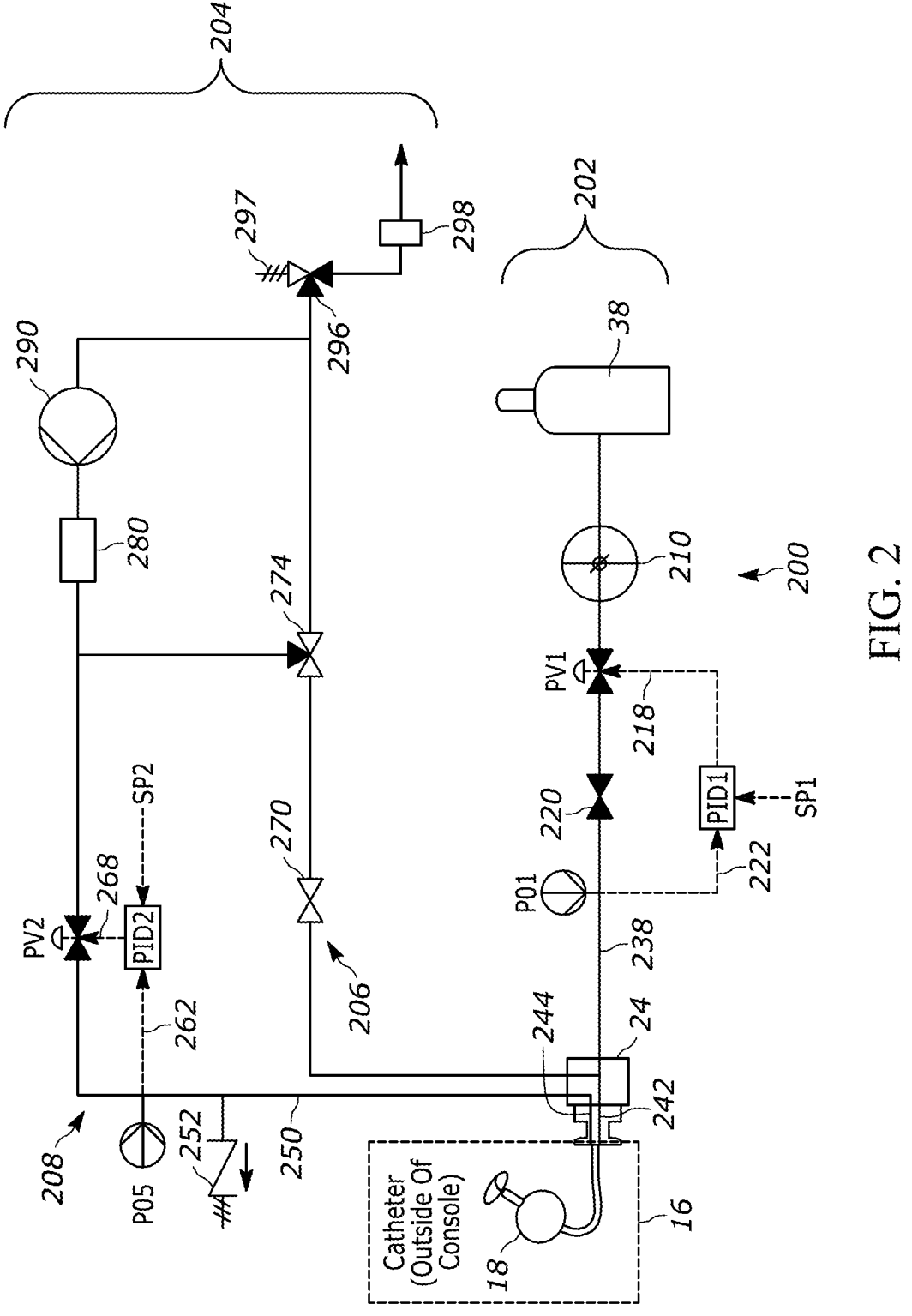
FIG. 2 is a block diagram illustrating a refrigerant delivery subsystem of the medical system of FIG. 1 according to various examples.

FIG. 2 is a block diagram illustrating a refrigerant delivery subsystem 200 of the system 10 according to various examples. The subsystem 200 includes a refrigerant injection path 202 and a refrigerant removal path 204. The refrigerant injection path 202 connects the tank 38 to an injection lumen 242 of the coaxial connector 24. As already indicated above, the injection lumen 242 of the coaxial connector 24 can be connected to a flow path within the elongated body 26 of the catheter 16, which delivers the refrigerant to the inflatable portion 18 (also see FIG. 1). The refrigerant removal path 204 connects a vacuum lumen 244 of the coaxial connector 24 to a three-way valve 296. As already indicated above, the vacuum lumen 244 of the coaxial connector 24 can be connected to another flow path within the elongated body 26 of the catheter 16, which removes the refrigerant from the inflatable portion 18 (also see FIG. 1). The three-way valve 296 can be operated to either exhaust the refrigerant from the path 204 that includes a branch 206 (vent line) and a branch 208 (vacuum line) through an exhaust port 297 (to atmosphere) or direct the refrigerant to external exhaust connected to a scavenging port 298.

In the example shown, the refrigerant injection path 202 includes a pressure regulator 210, a proportional (e.g., solenoid) valve PV1, and a two-way valve 220. The pressure regulator 210 is adjustable to limit the maximum pressure that can be applied to the proportional valve PV1 by the refrigerant flowing thereto from the tank 38. The state of the proportional valve PV1 is controlled via a control signal 218. A proportional-integral-derivative (PID) controller PID1 operates to generate the control signal 218 based on a pressure measurement 222 received from a pressure sensor P01 and further based on a setpoint signal SP1. The setpoint signal SP1 sets the target pressure for a delivery line segment 238 connected between the two-way valve 220 and the coaxial connector 24 and can be programmed (e.g., fixed or changed) via the electronic controller 40 and/or the console 12. The difference between the pressure measurement 222 and the setpoint signal SP1 defines an error signal for the PID controller PID1. The PID controller PID operates to generate the control signal 218 as a sum of three components determined based on the error signal. The first component is proportional to the error signal itself. The second component is proportional to the integral of the error signal. The third component is proportional to the time derivative of the error signal (also see Eq. (1)). The two-way valve 220 is used to allow or stop the refrigerant flow into the delivery line segment 238 as needed. For example, some commercially available proportional valve models that can be used to implement the proportional valve PV1 exhibit insufficient tightness in the OFF state thereof, thereby causing some refrigerant leakage therethrough. In such cases, the two-way valve 220 is switched into the OFF state to prevent the leaked refrigerant from reaching the delivery line segment 238.

In the example shown, the refrigerant removal path 204 includes the branches 206, 208, both of which are end-connected to the same input port of the three-way valve 296 at the respective second ends thereof. The first end of the branch 206 is directly connected to the delivery line 238. The first end of the branch 208 is directly connected to the vacuum lumen 244 of the coaxial connector 24.

In the example shown, the branch 208 of the refrigerant removal path 204 includes a proportional (e.g., solenoid) valve PV2, a flow meter 280, and a vacuum pump 290. The state of the proportional valve PV2 is controlled via a control signal 268. A PID controller PID2 operates to generate the control signal 268 based on a pressure measurement 262 received from a pressure sensor P05 and further based on a setpoint signal SP2. The setpoint signal SP2 sets the target pressure for an outflow line 250 connected between the vacuum lumen 244 of the coaxial connector 24 and the proportional valve PV2 and can be programmed (e.g., fixed or changed) via the electronic controller 40 and/or the console 12. The difference between the pressure measurement 262 and the setpoint signal SP2 defines an error signal for the PID controller PID2. The PID controller PID2 generates the control signal 268 based on this error signal in a manner similar to that described above in reference to the PID controller PID1, i.e., as a sum of three components proportional to the error signal, a time derivative of the error signal, and an integral of the error signal, respectively. A check valve 252 connected to the outflow line 250 is configured to vent out excess refrigerant when the refrigerant pressure in the outflow line 250 exceeds a threshold pressure value.

In the example shown, the branch 206 of the refrigerant removal path 204 includes a two-way valve 270 and a three-way valve 274. The two-way valve 270 is used to allow or stop the refrigerant outflow from the delivery line 238 through the branch 206 as needed. When the two-way valve 270 is in the ON (open) state, the three-way valve 274 can be used to direct the refrigerant flow received therefrom to the input port of the three-way valve 296 directly or through the pump 290. In the latter configuration of the three-way valve 274, a higher flow rate can be achieved than in the former configuration due to the suction applied to the branch 206 by the pump 290. In some examples, the two-way valves 220, 270 and the three-way valves 274, 296 are solenoid valves.

In some examples, the electronic controller 40 and/or the console 12 are configured to receive streams of measurements from the flow meter 280, pressure sensors P01, P05, and 88 (also see FIG. 1), and various temperature sensors located throughout the system 10. The electronic controller 40 and/or the console 12 are further configured to dynamically control the magnitude of the setpoint signals SP1 and SP2, thereby exerting parametric control over operations of the proportional valves PV1 and PV2. The electronic controller 40 and/or the console 12 are further configured to control the switching of the two-way valves 220 and 270 and the configurations of the three-way valves 274 and 296. The aforementioned control functions beneficially enable the electronic controller 40 and/or the console 12 to implement smooth and efficient inflation of the inflatable portion 18 to a target pressure and then achieve and maintain a desired refrigerant flow rate through the inflatable portion 18 in accordance with the intended medical procedure (such as cryoablation or cryomapping) while avoiding or reducing detrimental pressure and/or temperature variations. Several illustrative examples of leveraging these control functions toward optimally achieving the pertinent clinical objectives are described below in reference to FIGS. 3A-3B, 4A-4B, and 5A-5B.

Figures 3A, 3B:
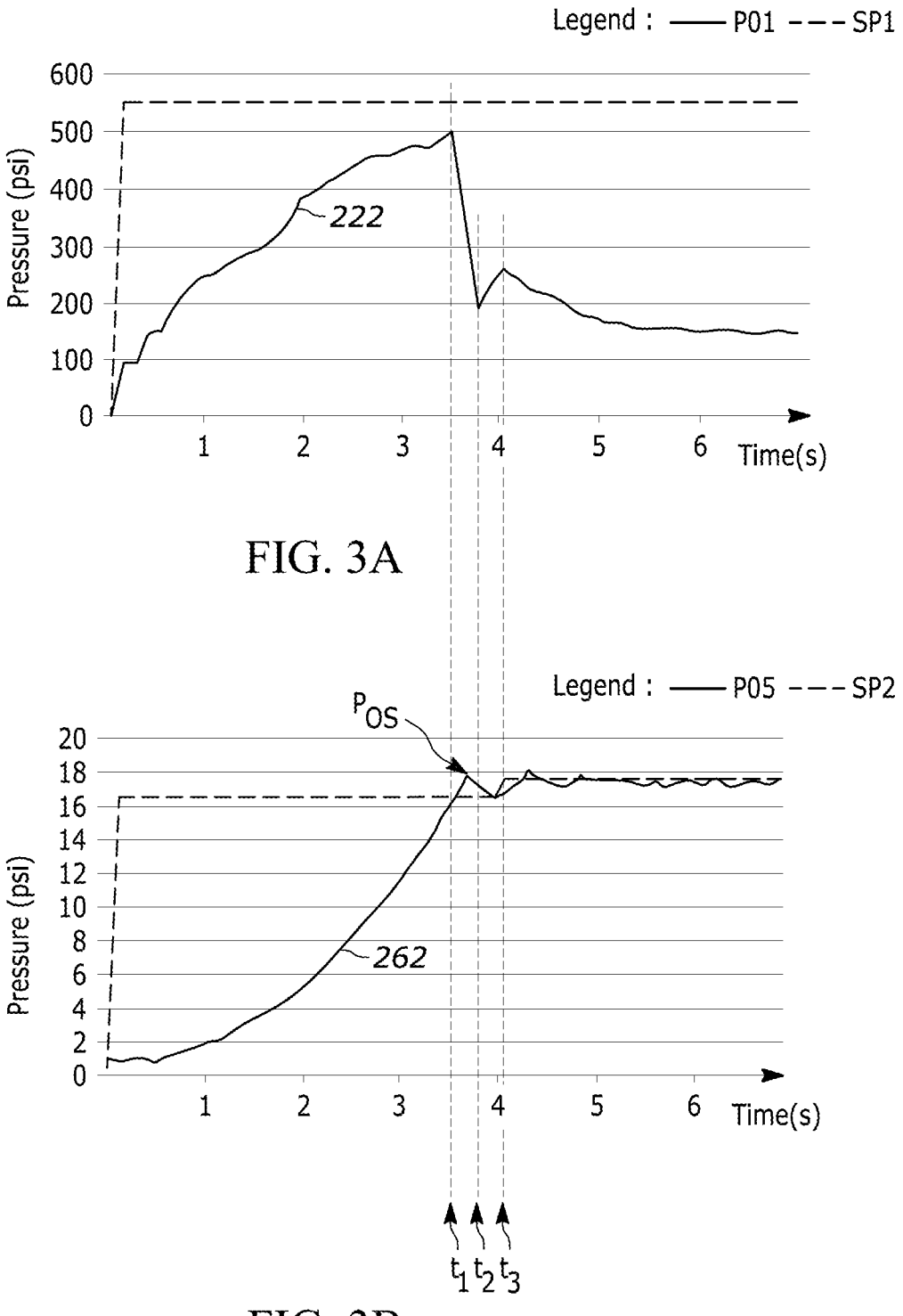
FIGS. 3A-3B graphically illustrate operations of the refrigerant delivery subsystem of FIG. 2 according to one example.

FIGS. 3A-3B graphically illustrate operations of the refrigerant delivery subsystem 200 according to one example. FIG. 3A graphically shows pressure settings and pressure measurements corresponding to the refrigerant injection path 202. FIG. 3B graphically shows pressure settings and pressure measurements corresponding to the branch 208 of the refrigerant removal path 204 during the same time interval of approximately seven seconds as that displayed in FIG. 3A. This specific example illustrates a beneficial ability of the subsystem 200 to provide fast (in approximately four seconds) inflation of the inflatable portion 18 of the catheter 16 to the target pressure of approximately 18 psi without generating a significant pressure overshoot. Significant pressure overshoots are generally undesirable but nevertheless are sometimes observed in at least some conventional refrigerant delivery systems.

At time t=0, the electronic controller 40 and/or the console 12 set(s) the values of the setpoint signals SP1 (FIG. 3A) and SP2 (FIG. 3B) to 550 psi and 16 psi, respectively, and opens the two-way valve 220. The relatively high value of SP1 is selected to shorten the inflation time. Note that the SP2 value (16 psi) at time t=0 is selected to be smaller than the target pressure of approximately 18 psi to help mitigate a pressure overshoot as explained in more detail below.

In response to SP1 being larger than the pressure measurement 222 at time t=0, the PID controller PID1 operates the proportional valve PV1 using the control signal 218 having a relatively high duty cycle, thereby causing the pressure in the delivery line 238 to increase rapidly as indicated by the curve 222 in FIG. 3A, which represents the stream of pressure measurements 222 produced by the pressure sensor P01. The rapidly increasing pressure in the delivery line 238 causes the refrigerant to flow into the inflatable volume 18 and then into the outflow line 250, thereby rapidly increasing the respective pressures in both. The pressure increase in the outflow line 250 follows the curve 262, which represents in FIG. 3B a stream of pressure measurements 262 produced by the pressure sensor P05.

At time t=$t_1$, the curve 262 reaches the level of the setpoint signal SP2 ($\approx$16 psi). In response to this event, the electronic controller 40 and/or the console 12 open(s) the two-way valve 270, which allows the refrigerant to flow directly from the delivery line 238 into the branch 206 of the refrigerant removal path 204. The electronic controller 40 and/or the console 12 also operate(s) to close the two-way valve 220 prior to opening the two-way valve 270 to prevent further increases in the refrigerant pressure in the delivery line 238. As a result, the refrigerant pressure in the delivery line 238 begins to drop precipitously, as indicated by the section of the curve 222 that follows the time t=$t_1$ (see FIG. 3A). This pressure drop dampens the overshoot of the setpoint signal SP2 ($\approx$16 psi) to a relatively small value, which is represented in FIG. 3B by a local peak (labeled $P_{OS}$) of the curve 262. At time t=$t_2$, the curve 222 (FIG. 3A) reaches a threshold value of 200 psi, which causes the electronic controller 40 and/or the console 12 to close the two-way valve 270. The closure of the two-way valve 270 disconnects the delivery line 238 from the branch 206, thereby causing the refrigerant pressure in the delivery line 238 to start to rise again as indicated by the section of the curve 222 that follows the time t=$t_2$ (FIG. 3A).

At time t=$t_3$, the electronic controller 40 and/or the console 12 operate(s) to increase the SP2 value from approximately 16 psi to the final target value of approximately 18 psi (see FIG. 3B). This SP2 increase is triggered by the decay of the overshoot peak $P_{OS}$ back down to the initial SP2 level of 16 psi. The SP2 increase causes the PID controller PID2 to close the proportional valve PV2 and then operate the proportional valve PV2 such that the curve 262 levels off at the final target value of approximately 18 psi. At time t>t₃, the decay rate of the curve 222 is relatively small (see FIG. 3A) due to the relatively stable refrigerant pressure in the outflow line 250 (see FIG. 3B) and the relatively small flow rate of the refrigerant moving from the delivery line 238, through the inflatable volume 18, into the outflow line 250.

Note that the above-described sequence of operations implemented by the electronic controller 40 and/or the console 12 in response to the various pressure measurements and timing events has two beneficial effects on the pressure overshoot represented by the peak $P_{OS}$. First, the sequence of operations shifts the base line of the pressure overshoot down to 16 psi due to the smaller initial value of SP2. Second, the sequence of operations aggressively manages the refrigerant pressure in the delivery line 238 by appropriately switching the various valves, including the two-way valves 220 and 270. As a result, the refrigerant pressure (the curve 262, FIG. 3B) in the outflow line 250 beneficially exhibits substantially no pressure overshoot with respect to the final target pressure of 18 psi.

Figures 4A, 4B:
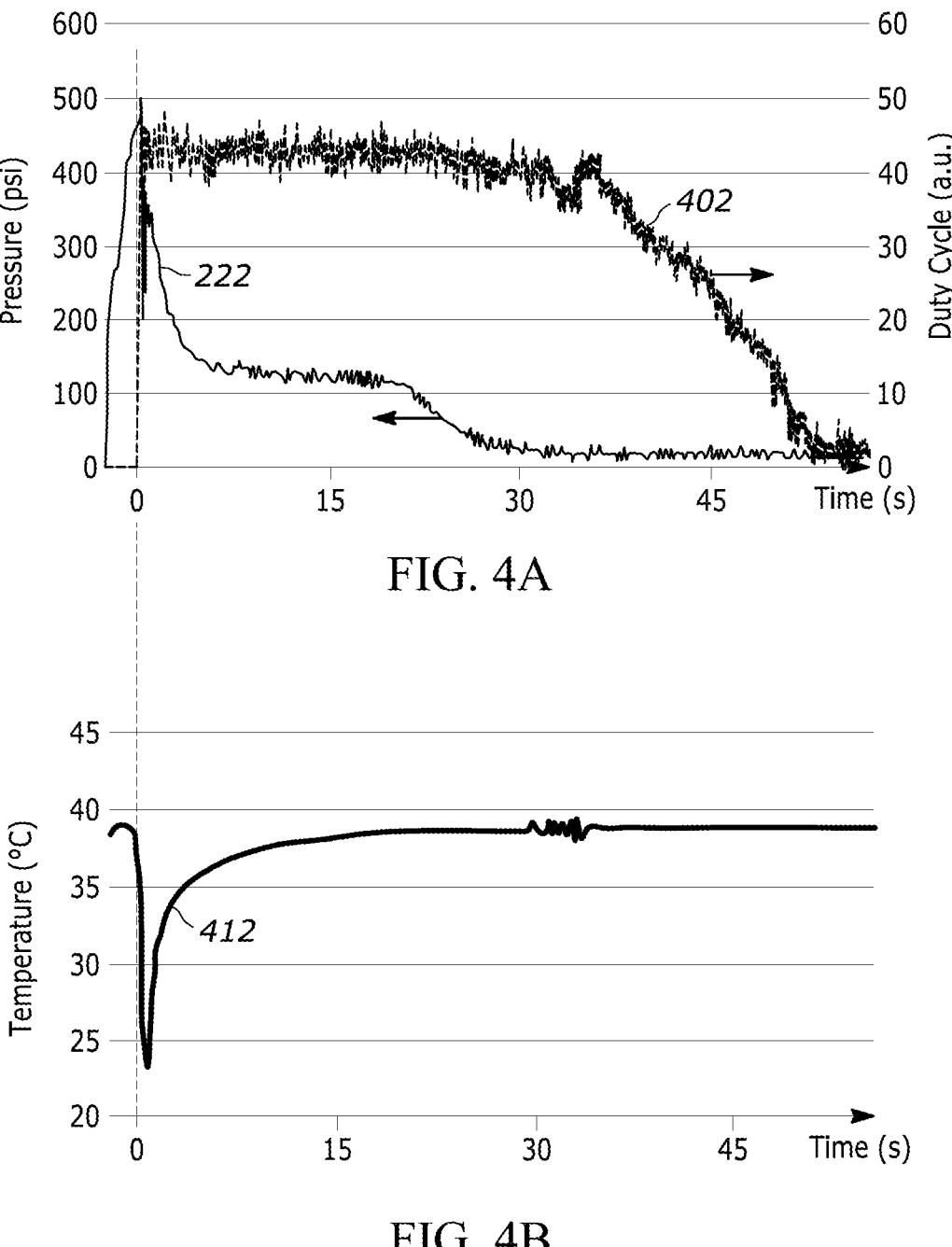
FIGS. 4A-4B graphically illustrate operations of the refrigerant delivery subsystem of FIG. 2 according to another example.

FIGS. 4A-4B graphically illustrate operations of the refrigerant delivery subsystem 200 according to another example. Therein, FIG. 4A graphically shows the pressure measurements 222 and the duty cycle of the proportional valve PV2 as a function of time. A curve 402 in FIG. 4A represents the duty cycle values. FIG. 4B graphically shows the temperature in the inflatable portion 18 during the same time interval as that of FIG. 4A. A curve 412 in FIG. 4B represents the temperature values. This specific example illustrates a beneficial ability of the subsystem 200 to maintain the pressure in the inflatable portion 18 at a fixed value of approximately 3 psig for a relatively long time on a single charge of the refrigerant in the delivery line segment 238, i.e., without reopening the two-way valve 220 and the proportional valve PV1 to recharge the delivery line segment 238 with a new volume of refrigerant drawn from the tank 38. In some examples, such a recharge of the delivery line 238 can be performed if deemed appropriate for the patient and/or the medical procedure.

In the example shown, operations of the subsystem 200 within a four-second time interval centered on the time t=0 are similar to those described above in reference to FIGS. 3A-3B. At the time t=0, the subsystem 200 starts to operate the proportional valve PV2 to maintain the pressure in the inflatable portion 18 at approximately 3 psig (or approximately 18 psi). In different configurations, the pressure in the inflatable portion 18 can be measured using the pressure sensor 88 (FIG. 1) or assumed to be approximately the same as the measurement 262 (FIG. 2).

A relatively high value of the duty cycle represents a situation in which the proportional valve PV2 spends more time in the open state than in the closed state. On the other hand, a relatively low value of the duty cycle represents a situation in which the proportional valve PV2 spends more time in the closed state than in the open state. The duty cycle of zero represents the continuously closed state of the proportional valve PV2. The curve 402 indicates how the duty cycle of the proportional valve PV2 gradually decreases as the pressure of the residual refrigerant in the delivery line segment 238 drops (see FIG. 4A). The temperature excursion in the inflatable portion 18 is largely time confined to the initial five seconds, and the amplitude of the temperature excursion is approximately fourteen degrees (see FIG. 4B). These characteristics of the temperature excursion beneficially present acceptable performance for certain clinical applications, as the time duration and temperature excursion level do not present a risk of thermal alteration of cells.

In some examples, introduction of the refrigerant into the catheter 16, when a particular treatment, such as ablation, is requested, may cause sudden pressure and/or temperature variations. In some cases, such variations may go beyond the acceptable limits that are programmed into the various control circuits within the system 10 or the subsystem 200. Detecting the rate of change of any refrigerant injection pressure in the console 12 and the time it takes to move the refrigerant from the subsystem 200 to the inflatable portion 18, which is referred to as the "transit time," may be used to provide additional degree of pressure stability and control when there are operating mode changes in the system 10, e.g., as described in more detail below.

In some embodiments, the PID controllers PID1 and PID2 are (re)programmed to further improve the pressure stability and controllability in the system 10. Eq. (1) provides an example mathematical expression used for this purpose:

$$u(t) = k_P e(t) + k_{I_p} \int_o^T e(t) dt + k_{Dp} \frac{de(t)}{dt} + k_{Dj} \frac{dP_{inj}(t - t_1)}{dt} S(t) \qquad (1)$$

where u(t) is the controller output (e.g., 218 or 268, FIG. 2); t is time; e (t) is the error signal; $P_{inj}$ is the injection pressure; S(t) is a bilevel function that can be switched by the controller(s) between the values of 0 and 1; and $k_P$, $k_{Ip}$, $k_{Dp}$, $k_{Dj}$, and $t_1$ are parameters. The first three terms of Eq. (1) represent the above-described three components of the control function determined based on the error signal, which are proportional to the error signal itself, the integral of the error signal, and the time derivative of the error signal, respectively. The fourth term of Eq. (1) is an additional component included into the controller output in accordance with some embodiments.

The parameter $t_1$ represents the time delay inherent in the subsystem 200 and reflects the combined transit time and phase-change time for the refrigerant injected into the catheter 16. The value of $t_1$ typically depends on the type and/or model of the catheter 16, and the values of $t_1$ corresponding to different types/models of the catheter 16 are stored in the memory 46 of the electronic controller 40 and/or the console 12 (FIG. 1). When S(t)=0, the fourth term of Eq. (1) is nulled. For operational phases where the injection pressure ($P_{inj}$) is expected to change, S(t) is changed to 1, which activates the fourth term of Eq. (1) in order to provide anticipatory information to the PID controller(s). The fourth term of Eq. (1), which is proportional to the time derivative $$\frac{dP_{inj}(t - t_1)}{dt},$$

is typically significant during changes in the operating mode of the system 10 characterized by large or rapid changes in the injection pressure.

Figure 5A:
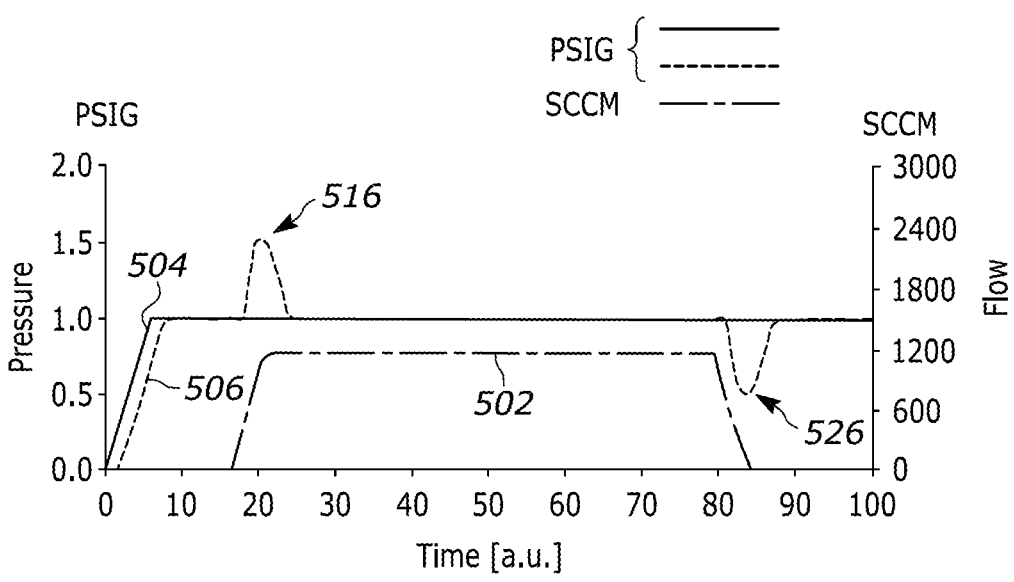
FIGS. 5A-5B graphically illustrate pressure disturbances in the refrigerant delivery subsystem of FIG. 2 according to some examples.
Figure 5B:
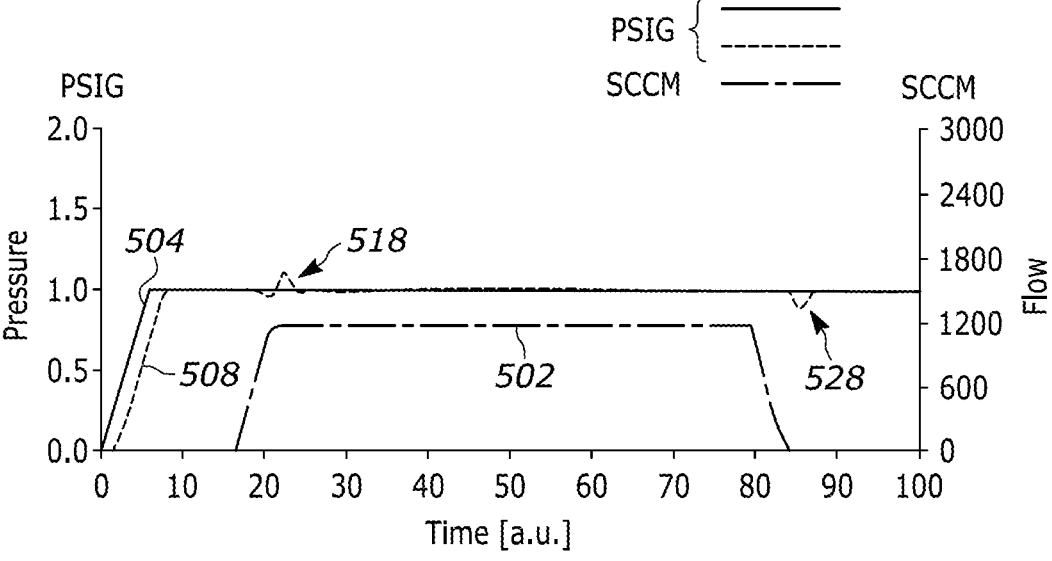

FIGS. 5A-5B graphically illustrate pressure disturbances observed in the subsystem 200 according to two examples. In both examples, the pressure disturbances are caused by changes in the refrigerant flow rate through the inflatable volume 18 corresponding to a flow rate curve 502. A curve 504 is a reference curve indicating an intended pressure profile in the inflatable volume 18. The subsystem 200 will typically exhibit the pressure profile similar to the curve 504 under substantially zero-flow conditions or under steady (constant) flow conditions. Curves 506 (FIG. 5A) and 508 (FIG. 5B) illustrate the pressure profiles exhibited by the subsystem 200 in response to the flow rate changes corresponding to the curve 502 for S(t)=0 and S(t)=1, respectively.

Referring now to FIG. 5A, the curve 506 has two significant pressure disturbances, i.e., a positive pressure disturbance 516 and a negative pressure disturbance 526. The positive pressure disturbance 516 is caused by the flow rate changes corresponding to the leading edge of the curve 502. The negative pressure disturbance 526 is caused by the flow rate changes corresponding to the trailing edge of the curve 502.

Referring to FIG. 5B, the curve 508 similarly has two pressure disturbances, i.e., a positive pressure disturbance 518 and a negative pressure disturbance 528. The positive pressure disturbance 518 is similarly caused by the flow rate changes corresponding to the leading edge of the curve 502, and the negative pressure disturbance 528 is similarly caused by the flow rate changes corresponding to the trailing edge of the curve 502. Comparison of FIGS. 5A and 5B reveals that the pressure disturbances 518, 528 are weaker than the pressure disturbances 516, 526. The beneficial attenuation of the pressure disturbances in the example of FIG. 5B is caused by the change of S(t) from S(t)=0 to S(t)=1, which activates the above-described fourth term in the control function used to generate the control signal 268.

Figure 6:
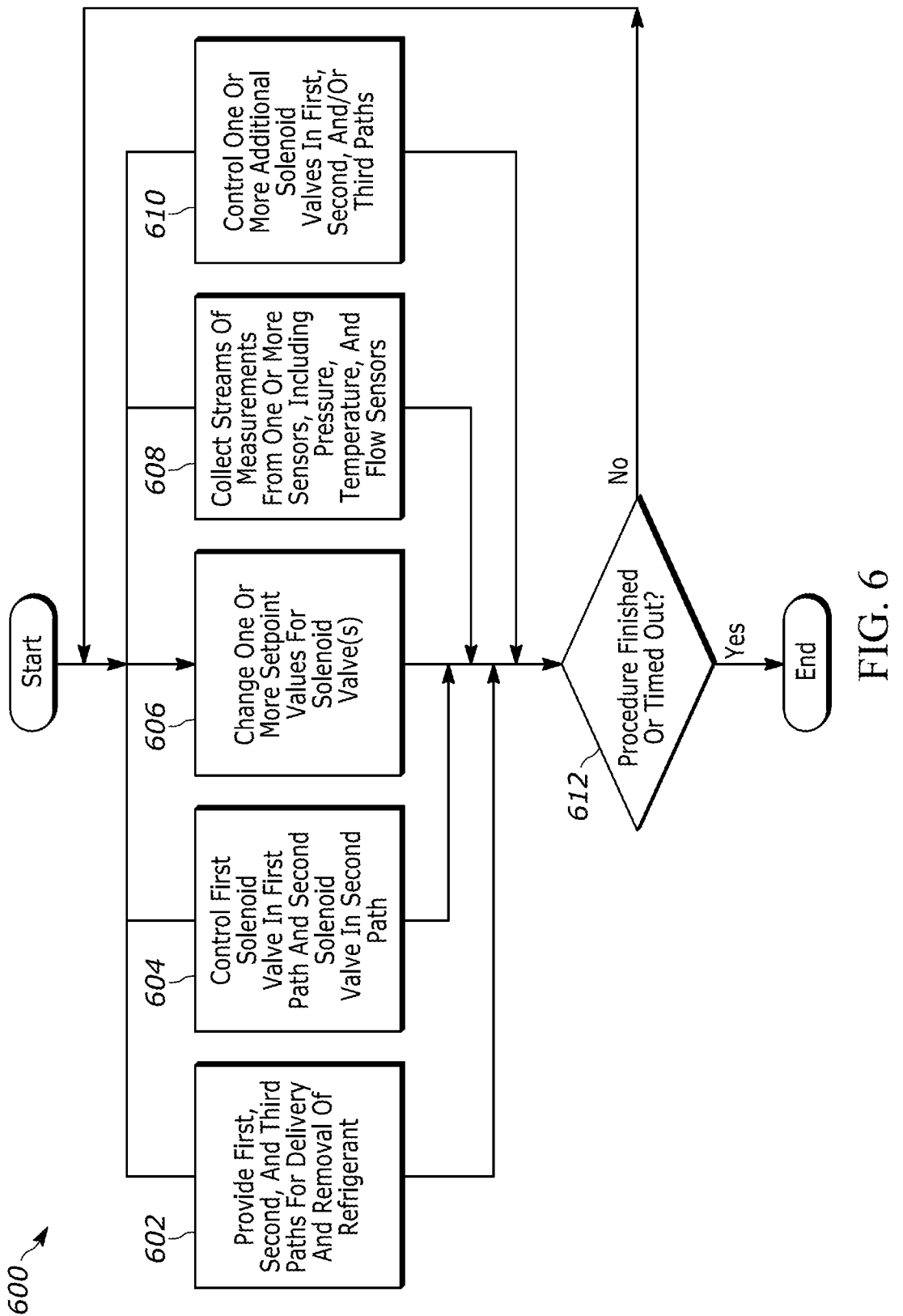
FIG. 6 is a flowchart illustrating a method of delivering refrigerant to a medical device, e.g., to the catheter connected to the refrigerant delivery subsystem of FIG. 2 in the medical system of FIG. 1, according to various examples.

FIG. 6 is a flowchart illustrating a method 600 of delivering refrigerant to a medical device, e.g., the catheter 16, according to some examples. The method 600 includes operations of blocks 602, 604, 606, 608, 610, and 612. In various examples, various subsets of operations of the blocks 602, 604, 606, 608, and 610 are performed sequentially, in parallel to one another, independent of one another, or in an interdependent or intercorrelated manner. In some examples, one or more processing loops involving different paths through the blocks 602, 604, 606, 608, and 610 and further through the decision block 612 are implemented and executed concurrently or consecutively during a medical procedure.

Operations of the block 602 include providing a first path (e.g., the refrigerant injection path 202, FIG. 2) for delivering the refrigerant to the inflatable portion 18 of the medical device 16 from a refrigerant source (e.g., the tank 38). The first path includes a first proportional valve (e.g., the proportional valve PV1). Operations of the block 602 also include providing a second path (e.g., the branch 208 of the refrigerant removal path 204, FIG. 2) for removing the refrigerant from the inflatable portion 18. The second path includes a second proportional valve (e.g., the proportional valve PV2) and a vacuum pump (e.g., the pump 290) connected to draw the refrigerant from the inflatable portion 18 through the second proportional valve. Operations of the block 602 also include providing a third path (e.g., the branch 206 of the refrigerant removal path 204, FIG. 2) end-connected at a first end thereof to a section (e.g., 238, FIG. 2) of the first path downstream from the first proportional valve. The third path includes a first valve (e.g., the two-way valve 270, FIG. 2) and a second valve (e.g., the three-way valve 274, FIG. 2).

Operations of the block 604 include controlling, with a control circuit (e.g., a combination of PID1, PID2, 40, 12, FIGS. 1-2), the first proportional valve based on a pressure measurement (e.g., 222, FIG. 2) in the first path and further based on a first setpoint value (e.g., SP1, FIG. 2). Operations of the block 604 also include controlling, with the control circuit, the second proportional valve based on a pressure measurement in the second path (e.g., the measurement 262, FIG. 2) or a pressure measurement in the inflatable portion (e.g., the measurement by the pressure sensor 88, FIG. 1) and further based on a second setpoint value (e.g., SP2, FIG. 2). In some examples, operations of the block 604 also include operating, with the control circuit, the first or second proportional valve based on a sum of a respective plurality of terms including a first term proportional to an error signal, a second term proportional to an integral of the error signal, a third term proportional to a derivative of the error signal, and a term proportional to a derivative of the pressure measurement in the first path at an earlier time (see, e.g., Eq. (1)). In some configurations, the fourth term is nulled.

Operations of the block 606 include changing, with the control circuit, one or both of the first and second setpoint values. One nonlimiting example of such changing is described above in reference to FIG. 3B. Another nonlimiting example of such changing includes selecting the first and/or second setpoint values based on the make and model of the medical device 16.

Operations of the block 608 include collecting, with the control circuit, streams of measurements from a set of sensors variously distributed throughout the system 10. In various examples, the set of sensors is selected from the group consisting of: a first pressure sensor (e.g. P01, FIG. 2) in the first path, a second pressure sensor (e.g. P05, FIG. 2) in the second path, a third pressure sensor (e.g., 88, FIG. 1) in the inflatable portion 18, a temperature sensor (e.g., 89, FIG. 1) in the inflatable portion 18, and a flow meter (e.g., 280, FIG. 2) in the second path.

Operations of the block 610 include controlling, with the control circuit, various pressure valves in the subsystem 200 based on the stream of measurements collected from the applicable set of sensors. In various examples, the controlled pressure valves include some or all of the two-way valves 220 and 270 and the three-way valves 274 and 296.

The decision block 612 is used to control the exit from the various processing and control loops of the method 600. In some examples, such exit is tied to the medical procedure that is being performed. When the medical procedure is still ongoing ("No" at the decision block 612), the pertinent ones of the various processing and control loops of the method 600 continue to be executed. When the medical procedure is finished ("Yes" at the decision block 612), the method 600 is terminated.

According to one example disclosed above, e.g., in the summary section and/or in reference to any one or any combination of some or all of FIGS. 1-6, provided is a system for delivering refrigerant to a medical device, the system comprising: a first path for delivering the refrigerant to an expansion cavity portion of the medical device from a refrigerant source, the first path including a first solenoid valve; a second path for removing the refrigerant from the expansion cavity portion, the second path including a second solenoid valve and a vacuum pump connected to draw the refrigerant from the expansion cavity portion through the second solenoid valve; and a control circuit including: a first controller to control the first solenoid valve based on a pressure measurement in the first path and further based on a first setpoint value, and a second controller to control the second solenoid valve based on a pressure measurement in the second path or in the expansion cavity portion and further based on a second setpoint value.

Herein, the term "expansion cavity portion" refers to a volume in the medical device into which the refrigerant is allowed to expand. In some examples, the expansion cavity portion is similar to the inflatable portion 18 (FIG. 1). In some other examples, the expansion cavity portion is in a rigid distal tip of the catheter that may be similar to the tip 36 (FIG. 1). The latter type of expansion cavities is encountered, e.g., in focal or mapping catheters.

In some examples of the above system, the medical device comprises a cryoablation or cryomapping catheter; and wherein the expansion cavity portion is an inflatable portion of the cryoablation or cryomapping catheter.

In some examples of any of the above systems, the first controller is configured to operate the first solenoid valve based on a sum of a first plurality of terms including a term proportional to a first error signal, a term proportional to an integral of the first error signal, and a term proportional to a derivative of the first error signal, the first error signal representing a difference between the pressure measurement in the first path and the first setpoint value.

In some examples of any of the above systems, the second controller is configured to operate the second solenoid valve based on a sum of a second plurality of terms including a term proportional to a second error signal, a term proportional to an integral of the second error signal, and a term proportional to a derivative of the second error signal, the second error signal representing a difference between the pressure measurement in the second path and the second setpoint value.

In some examples of any of the above systems, the second plurality of terms further includes a term proportional to a derivative of the pressure measurement in the first path at an earlier time.

In some examples of any of the above systems, the second controller is configured to operate the second solenoid valve based on a sum of a plurality of terms including a term proportional to an error signal, a term proportional to an integral of the error signal, a term proportional to a derivative of the error signal, and a term proportional to a derivative of the pressure measurement in the first path at an earlier time, the error signal being a difference between the pressure measurement in the second path and the second setpoint value.

In some examples of any of the above systems, the control circuit is configured to change the second setpoint value when the expansion cavity portion is being filled with the refrigerant supplied through the first path.

In some examples of any of the above systems, the system further comprises a third path end-connected at a first end thereof to a section of the first path downstream from the first solenoid valve, the third path including a third solenoid valve, wherein the control circuit is configured to open the third solenoid valve to vent the refrigerant from the first path.

In some examples of any of the above systems, the third path further includes a fourth solenoid valve between a second end thereof and the third solenoid valve, wherein the control circuit is configured to operate the fourth solenoid valve to selectively connect the vacuum pump to the third path.

In some examples of any of the above systems, the control circuit includes an electronic controller connectable to a set of sensors selected from the group consisting of a first pressure sensor in the first path, a second pressure sensor in the second path, a third pressure sensor in the expansion cavity portion, a temperature sensor in the expansion cavity portion, and a flow meter in the second path.

In some examples of any of the above systems, the system further comprises a third path end-connected at a first end thereof to a section of the first path downstream from the first solenoid valve, the third path including a third solenoid valve and a fourth solenoid valve, wherein the electronic controller is configured to operate the third solenoid valve and the fourth solenoid valve based on a stream of measurements by the set of sensors.

In some examples of any of the above systems, the refrigerant comprises nitrous oxide.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. A system for delivering refrigerant to a medical device, the system comprising:

a first path for delivering the refrigerant to an expansion cavity portion of the medical device from a refrigerant source, the first path including a first solenoid valve;

a second path for removing the refrigerant from the expansion cavity portion, the second path including a second solenoid valve and a vacuum pump connected to draw the refrigerant from the expansion cavity portion through the second solenoid valve; and a control circuit including:

a first controller to control the first solenoid valve based on a pressure measurement in the first path and further based on a first setpoint value, and a second controller to control the second solenoid valve based on a pressure measurement in the second path or in the expansion cavity portion and further based on a second setpoint value, wherein the first controller is configured to operate the first solenoid valve based on a sum of a first plurality of terms including a term proportional to a first error signal, a term proportional to an integral of the first error signal, and a term proportional to a derivative of the first error signal, the first error signal representing a difference between the pressure measurement in the first path and the first setpoint value.

2. The system of claim 1, wherein the medical device comprises a cryoablation or cryomapping catheter; and wherein the expansion cavity portion is an inflatable portion of the cryoablation or cryomapping catheter.

3. The system of claim 1, wherein the second controller is configured to operate the second solenoid valve based on a sum of a second plurality of terms including a term proportional to a second error signal, a term proportional to an integral of the second error signal, and a term proportional to a derivative of the second error signal, the second error signal representing a difference between the pressure measurement in the second path and the second setpoint value.

4. The system of claim 3, wherein the second plurality of terms further includes a term proportional to a derivative of the pressure measurement in the first path at an earlier time.

5. The system of claim 1, wherein the control circuit is configured to change the second setpoint value when the expansion cavity portion is being filled with the refrigerant supplied through the first path.

6. The system of claim 1, further comprising a third path end-connected at a first end thereof to a section of the first path downstream from the first solenoid valve, the third path including a third solenoid valve, wherein the control circuit is configured to open the third solenoid valve to vent the refrigerant from the first path.

7. The system of claim 6, wherein the third path further includes a fourth solenoid valve between a second end thereof and the third solenoid valve, wherein the control circuit is configured to operate the fourth solenoid valve to selectively connect the vacuum pump to the third path.

8. The system of claim 1, wherein the control circuit includes an electronic controller connectable to a set of sensors selected from the group consisting of a first pressure sensor in the first path, a second pressure sensor in the second path, a third pressure sensor in the expansion cavity portion, a temperature sensor in the expansion cavity portion, and a flow meter in the second path.

9. The system of claim 8, further comprising a third path end-connected at a first end thereof to a section of the first path downstream from the first solenoid valve, the third path including a third solenoid valve and a fourth solenoid valve, wherein the electronic controller is configured to operate the third solenoid valve and the fourth solenoid valve based on a stream of measurements by the set of sensors.

10. The system of claim 1, wherein the refrigerant comprises nitrous oxide.

11. A method of delivering refrigerant to a medical device, the method comprising:

providing a first path for delivering the refrigerant to an expansion cavity portion of the medical device from a refrigerant source, the first path including a first solenoid valve;

providing a second path for removing the refrigerant from the expansion cavity portion, the second path including a second solenoid valve and a vacuum pump connected to draw the refrigerant from the expansion cavity portion through the second solenoid valve;

controlling, with a control circuit, the first solenoid valve based on a pressure measurement in the first path and further based on a first setpoint value;

controlling, with the control circuit, the second solenoid valve based on a pressure measurement in the second path or in the expansion cavity portion and further based on a second setpoint value; and operating, with the control circuit, the first solenoid valve based on a sum of a first plurality of terms including a term proportional to a first error signal, a term proportional to an integral of the first error signal, and a term proportional to a derivative of the first error signal, the first error signal representing a difference between the pressure measurement in the first path and the first setpoint value.

12. The method of claim 11, further comprising operating, with the control circuit, the second solenoid valve based on a sum of a second plurality of terms including a term proportional to a second error signal, a term proportional to an integral of the second error signal, and a term proportional to a derivative of the second error signal, the second error signal representing a difference between the pressure measurement in the second path and the second setpoint value.

13. The method of claim 12, wherein the second plurality of terms further includes a term proportional to a derivative of the pressure measurement in the first path at an earlier time.

14. The method of claim 11, further comprising operating, with the control circuit, the second solenoid valve based on a sum of a second plurality of terms including a term proportional to a second error signal, a term proportional to an integral of the second error signal, a term proportional to a derivative of the second error signal, and a term proportional to a derivative of the pressure measurement in the first path at an earlier time, the second error signal being a difference between the pressure measurement in the second path and the second setpoint value.

15. The method of claim 11, further comprising changing the second setpoint value when the expansion cavity portion is being filled with the refrigerant supplied through the first path.

16. The method of claim 11, wherein the control circuit is connectable to a set of sensors selected from the group consisting of a first pressure sensor in the first path, a second pressure sensor in the second path, a third pressure sensor in the expansion cavity portion, a temperature sensor in the expansion cavity portion, and a flow meter in the second path.

17. The method of claim 16, further comprising:

providing a third path end-connected at a first end thereof to a section of the first path downstream from the first solenoid valve, the third path including a third solenoid valve and a fourth solenoid valve; and operating, with the control circuit, the third solenoid valve and the fourth solenoid valve based on a stream of measurements by the set of sensors.

18. A system for delivering refrigerant to a medical device, the system comprising:

a first path for delivering the refrigerant to an expansion cavity portion of the medical device from a refrigerant source, the first path including a first solenoid valve;

a second path for removing the refrigerant from the expansion cavity portion, the second path including a second solenoid valve and a vacuum pump connected to draw the refrigerant from the expansion cavity portion through the second solenoid valve; and a control circuit including:

a first controller to control the first solenoid valve based on a pressure measurement in the first path and further based on a first setpoint value, and a second controller to control the second solenoid valve based on a pressure measurement in the second path or in the expansion cavity portion and further based on a second setpoint value, wherein the second controller is configured to operate the second solenoid valve based on a sum of a plurality of terms including a term proportional to an error signal, a term proportional to an integral of the error signal, a term proportional to a derivative of the error signal, and a term proportional to a derivative of the pressure measurement in the first path at an earlier time, the error signal being a difference between the pressure measurement in the second path and the second setpoint value.

\* \* \* \* \*